(12) United States Patent
Lee et al.

(10) Patent No.: US 9,417,212 B2
(45) Date of Patent: Aug. 16, 2016

(54) DEFECT INSPECTION DEVICE OF STEEL PLATE

(71) Applicant: POSCO, Pohang-si, Gyeongsangbuk-do (KR)

(72) Inventors: Ju-Seung Lee, Pohang-si (KR); Se-Ho Choi, Pohang-si (KR); Sang-Woo Choi, Pohang-si (KR); Jong-Pil Yun, Pohang-si (KR); Shin-Hwan Kang, Gwangyang-si (KR); Ki-Jang Oh, Pohang-si (KR)

(73) Assignee: POSCO, Pohang-Si, Gyeongsangbuk-Do (KR)

( * ) Notice: Subject to any disclaimer, the term of this patent is extended or adjusted under 35 U.S.C. 154(b) by 81 days.

(21) Appl. No.: 14/365,299

(22) PCT Filed: Nov. 30, 2012

(86) PCT No.: PCT/KR2012/010307
§ 371 (c)(1),
(2) Date: Jun. 13, 2014

(87) PCT Pub. No.: WO2013/089373
PCT Pub. Date: Jun. 20, 2013

(65) Prior Publication Data
US 2014/0347041 A1 Nov. 27, 2014

(30) Foreign Application Priority Data

Dec. 15, 2011 (KR) .................. 10-2011-0135319

(51) Int. Cl.
G01N 27/82 (2006.01)
G01N 27/87 (2006.01)
G01N 27/90 (2006.01)

(52) U.S. Cl.
CPC ............ *G01N 27/9033* (2013.01); *G01N 27/82* (2013.01); *G01N 27/87* (2013.01)

(58) Field of Classification Search
None
See application file for complete search history.

(56) References Cited

U.S. PATENT DOCUMENTS 6,057,684 A * 5/2000 Murakami ............ G01N 27/82
324/225
2002/0121896 A1 9/2002 Kato et al.
(Continued)

FOREIGN PATENT DOCUMENTS

JP 5-322851 12/1993
JP 5-322852 12/1993
(Continued)

OTHER PUBLICATIONS

Notice of Office Action Reasons for Rejection with English-language translation issued by Japanese Patent Office on Jul. 28, 2015 in corresponding Japanese Patent Application No. 2014-547086.
(Continued)

*Primary Examiner* — Jermele M Hollington
*Assistant Examiner* — Douglas X Rodriguez
(74) *Attorney, Agent, or Firm* — Finnegan Henderson Farabow Garrett & Dunner LLP

(57) ABSTRACT

Provided is a defect inspection device of a steel plate. The defect inspection device according to the present invention includes a plurality of inspection units arranged in a width direction of the steel plate, wherein each of the plurality of inspection units includes a first magnetized pole and a second magnetized pole corresponding to each other. Also, the inspection unit includes: a magnetizing part generating a magnetic flux for magnetizing the steel plate in a direction inclined at a predetermined angle with respect to a rolling direction through the first magnetized pole and the second magnetized pole; and a detection part detecting a leakage flux that leaks due to defects existing in or on the steel plate by using the flux generated by the magnetizing part. Thus, the defects may be correctly detected through the defect inspection device.

9 Claims, 9 Drawing Sheets

(56) References Cited

U.S. PATENT DOCUMENTS

| | | |
|---|---|---|
| 2011/0040499 A1 | 2/2011 | Koshihara et al. |
| 2011/0234212 A1* | 9/2011 | Lepage ............. G01N 27/82 |
| | | 324/219 |

FOREIGN PATENT DOCUMENTS

| | | |
|---|---|---|
| JP | 09-274016 | 10/1997 |
| JP | 09-304345 | 11/1997 |
| JP | 2007-322176 | 12/2007 |
| JP | 2009-265087 | 11/2009 |
| JP | 2010-048624 | 3/2010 |
| JP | 2011-7565 | 1/2011 |
| JP | 2011-196863 | 10/2011 |
| KR | 2002-0060681 | 7/2002 |
| KR | 10-2010-0076838 | 7/2010 |
| KR | 10-2011-0025282 | 3/2011 |

OTHER PUBLICATIONS

English-language International Search Report from the Korean Patent Office for International Application No. PCT/KR2012/010307, mailing date Mar. 12, 2013.

* cited by examiner

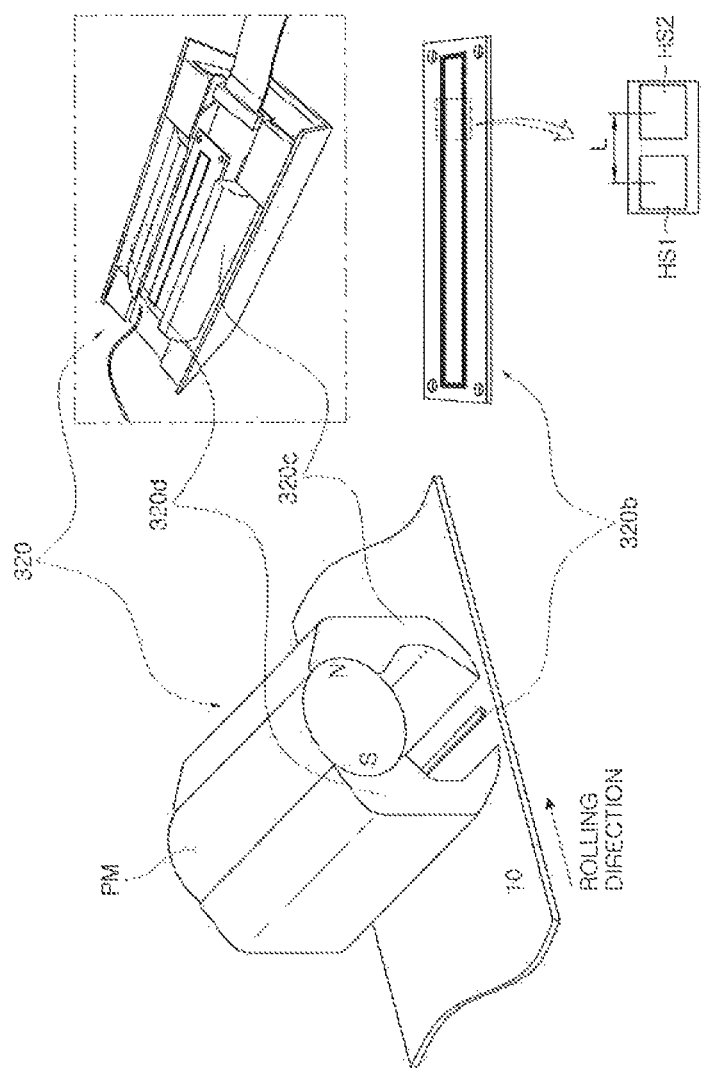

DEFECT INSPECTION DEVICE OF STEEL PLATE

TECHNICAL FIELD

The present disclosure relates to a device for inspecting defects present in an interior portion or a surface of a steel plate using a leakage magnetic flux.

BACKGROUND ART

Technologies for detecting defects in a steel plate may include an ultrasonic test, a magnetic flux leakage inspection, a magnetic particle inspection, an eddy-current inspection, an optical inspection method and the like.

Among these, a magnetic flux leakage inspection is a scheme of detecting a portion of magnetic flux leaked to the outside of a steel plate due to defects present in a steel plate when the steel plate is magnetized in a certain direction, using a magnetic sensor or a hall sensor. Such a magnetic flux leakage inspection may have superior performance in terms of the detection of crack defects occurring in a surface or below a surface layer of a ferromagnetic metal, and an example of an inspection device using the magnetic flux leakage described above is disclosed in Cited Document (Korean Patent Laid-Open Publication No. 2010-0076838).

Referring to FIG. 1 in connection with Korean Patent Laid-Open Publication No. 2010-0076838, a magnetizer 120 may be disposed on an upper portion of a steel plate 10 wound around a roll 110. Electromagnetic poles 121a and 121b are alternately arranged in a lower region of the magnetizer 120 and a coil 122 is wound on an upper region of the magnetizer 120. Here, in a case in which currents flow in the electromagnetic poles 121a and 121b through the coil 122 in opposite directions, the steel plate 10 may be magnetized in a direction from the electromagnetic pole 121a having N-polarity to the electromagnetic pole 121b having S-polarity. In this case, a leakage magnetic flux may be sensed by a sensor 131 disposed between the electromagnetic poles 121a and 121b, such that defects present in the steel plate 10 may be detected. Meanwhile, the electromagnetic poles 121a and 121b may be spaced apart from each other by a predetermined interval and be configured such that they are inclined at a certain angle ($\theta$) with respect to a rolling direction and thus, are formed to a boundary line A at which the steel plate 10 comes into contact with the roll 110, in a spiral manner.

However, according to the Cited Document, the following limitations are present.

First, as illustrated in FIG. 2, accurate detection of defects may be difficult due to a non-detection region R1 in which magnetic flux is unable to be detected. In magnetic flux formed in ends of the electromagnetic pole 121a having N-polarity and the electromagnetic pole 121b having S-polarity, directions and degrees of intensity thereof may not be uniformly formed (see reference numeral 201 and R2).

Second, as illustrated in FIG. 1, the magnetizer 120 may have an integrated structure in which a plurality of the electromagnetic poles 121a and 121b may be integrally provided. Therefore, it may be unfeasible to replace only some units such as the electromagnetic poles 121a and 121b or the sensor 131, leading to difficulties in terms of maintenance and management.

Third, since defects present in a surface and an interior portion of the steel plate 10 may be simultaneously detected, it may be difficult to separately detect a surface defect and an interior defect or accurately determining a position of the interior defect may be unfeasible.

DISCLOSURE

Technical Problem

An aspect of the present disclosure provides a device for inspecting defects in a steel plate, the device being capable of accurately detecting defects in surfaces or in interior portions of the steel plate.

An aspect of the present disclosure also provides a device for inspecting defects in a steel plate, the device allowing for efficient maintenance and management thereof.

An aspect of the present disclosure also provides a device for inspecting defects in a steel plate, the device being capable of separately detecting a surface defect and an interior defect or accurately determining a position of the interior defect.

Technical Solution

According to an aspect of the present disclosure, a defect inspection device for inspecting defects in a steel plate may include: a plurality of inspection units arranged in a width direction of the steel plate, wherein each of the plurality of inspection units includes a magnetizer including a first magnetized pole and a second magnetized pole corresponding to each other, and generating magnetic flux for magnetizing the steel plate in a direction inclined at a predetermined angle with respect to a rolling direction of the steel plate; and a detector detecting a leakage magnetic flux leaked due to defects present in an interior portion or a surface of the steel plate, using the magnetic flux generated by the magnetizer.

According to an aspect of the present disclosure, the second magnetized pole may be spaced apart from the first magnetized pole by a predetermined distance and disposed to be parallel to the first magnetized pole, in a direction perpendicular to a direction in which the first magnetized pole is inclined, and the first magnetized pole and the second magnetized pole may have the same length.

According to an aspect of the present disclosure, the first magnetized pole and the second magnetized pole may be inclined at an angle of 45 degrees with respect to the rolling direction.

According to an aspect of the present disclosure, the plurality of inspection units may be provided in modular form such that the inspection units are individually detachable.

According to an aspect of the present disclosure, the magnetizer may have a permanent magnet and a yoke extended to both sides of the permanent magnet, and the first magnetized pole may be provided on one end of the yoke and a second magnetized pole may be provided on the other end of the yoke.

According to an aspect of the present disclosure, the permanent magnet may be a cylindrical permanent magnet.

The cylindrical permanent magnet may be provided in the magnetizer such that the cylindrical permanent magnet rotates about an axis of a cylinder extended in a length direction of the cylinder, and a magnitude of the magnetic flux induced in the yoke may be adjustable.

According to an aspect of the present disclosure, the plurality of inspection units may include upper inspection units disposed on an upper portion of the steel plate; and lower inspection units disposed on a lower portion of the steel plate.

According to an aspect of the present disclosure, the defect inspection device may further include a defect analyzer analyzing a defect position in a thickness direction of the steel plate, based on a phase and a magnitude of a signal measured by each of the upper inspection units and lower inspection units.

According to an aspect of the present disclosure, the detector may include a plurality of hall sensors, an interval between the hall sensors adjacent to each other being 60 μm or less.

According to an aspect of the present disclosure, in the plurality of inspection units, the first and second magnetized poles may be disposed such that adjacent magnetized poles in the inspection units adjacent to each other are identical to each other.

Advantageous Effects

According to exemplary embodiments of the present disclosure, two magnetized poles configuring a magnetizer have the same length, such that accurate defect detection may be enabled.

According to exemplary embodiments of the present disclosure, a plurality of inspection units are provided in modular form such that the inspection units are individually detachable. Thus, maintenance and management efficiency of an inspection device may be increased.

According to exemplary embodiments of the present disclosure, the inspection units are disposed on both upper and lower portions of the steel plate to detect a leakage magnetic flux, a surface defect and an interior defect may be separately detected and a position of the interior defect may be accurately determined.

DESCRIPTION OF DRAWINGS

FIG. 4A is views illustrating an internal structure of an inspection unit according to an exemplary embodiment of the present disclosure.

BEST MODE

Figure 1:
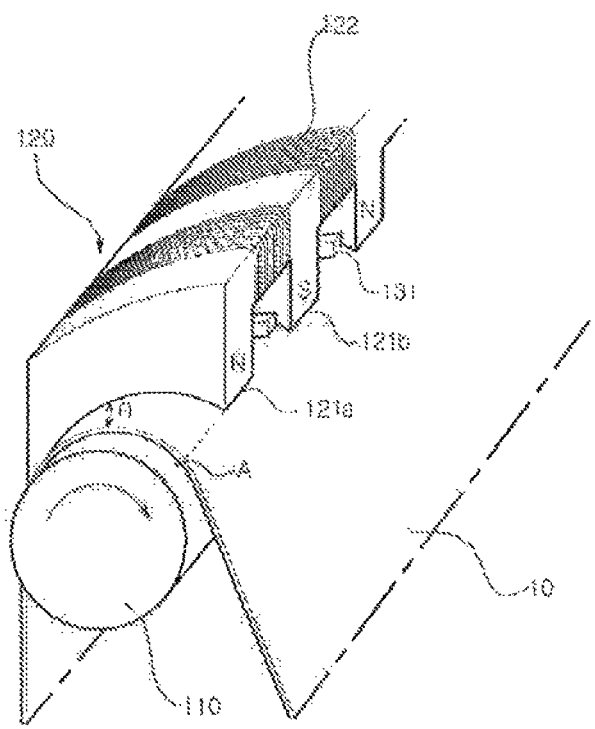
FIG. 1 is a view illustrating a structure of an inspection device according to the related art.
Figure 2:
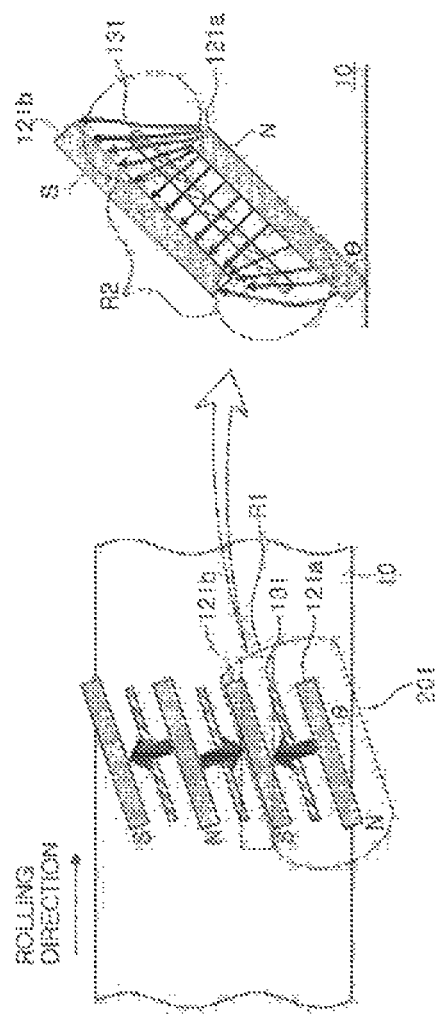
FIG. 2 is views illustrating the inspection device of FIG. 1 when viewed from the above, in order to describe limitations of the related art.

Hereinafter, exemplary embodiments of the present disclosure will now be described in detail with reference to the accompanying drawings. Exemplary embodiments of the present disclosure may, however, be exemplified in many different forms and should not be construed as being limited to the specific embodiments set forth herein. In the drawings, the shapes and dimensions of elements may be exaggerated for clarity, and the same reference numerals will be used throughout to designate the same or like elements.

Figure 3:
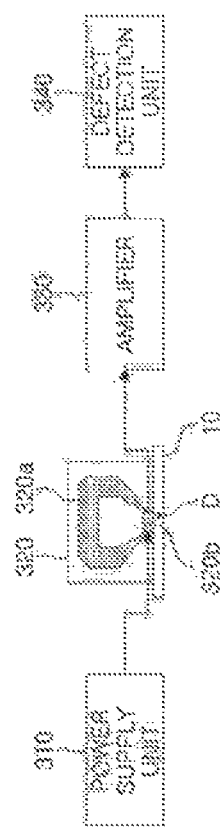
FIG. 3 is a configuration diagram of an inspection device according to an exemplary embodiment of the present disclosure.

FIG. 3 is a configuration diagram of an inspection device according to an exemplary embodiment of the present disclosure. The inspection device according to an exemplary embodiment of the present disclosure may include a power supply unit 310 supplying power to a detector 320b, a plurality of inspection units (a single inspection unit 320 is illustrated in FIG. 3) arranged in a width direction of a steel plate 10, an amplifier 330 amplifying a leakage magnetic flux detected by the inspection unit 320, and a defect detection unit 340 detecting defects (hereinafter, referred to as "defects D") present in the steel plate 10 based on the leakage magnetic flux amplified by the amplifier 330. Meanwhile, each of the plurality of inspection unit 320 may include a magnetizer 320a magnetizing the steel plate 10 in a predetermined direction and the detector 320b detecting the leakage magnetic flux due to the defects D in the steel plate 10.

Hereinafter, the inspection unit will be described in detail.

FIG. 4A is views illustrating an internal structure of a single inspection unit according to an exemplary embodiment of the present disclosure.

As illustrated in FIG. 4A, one inspection unit 320 may include a permanent magnet PM and a yoke extended to both sides of the permanent magnet PM. A first magnetized pole 320c may be provided on one end of the yoke and a second magnetized pole 320d may be provided on the other end of the yoke. The permanent magnet PM, a cylindrical permanent magnet, may be provided in the magnetizer 320a such that the permanent magnet PM may rotate about an axis of a cylinder extended in a length direction of the cylinder, and a magnitude of the magnetic flux induced in the yoke may be adjusted. That is, as the permanent magnet PM rotates about the axis of the cylinder extended in the length direction of the cylinder, a magnitude of magnetic flux formed between the first magnetized pole 320c and the second magnetized pole 320d may be varied.

By way of example, in a case in which N-pole and S-pole of the permanent magnet PM are vertically disposed, the lowest magnitude of magnetic flux is formed between the first magnetized pole 320c and the second magnetized pole 320d. In a case in which N-pole and S-pole of the permanent magnet PM are horizontally disposed, the highest magnitude of magnetic flux is formed between the first magnetized pole 320c and the second magnetized pole 320d. In addition, the first magnetized pole 320c and the second magnetized pole 320d may be disposed on an upper portion of the steel plate 10 in a direction inclined at a predetermined angle with respect to a rolling direction, and a description thereof will be provided below with reference to FIG. 4B.

Further, the detector 320b may be disposed between the first magnetized pole 320c and the second magnetized pole 320d in the length direction of the cylindrical permanent magnet PM, while being spaced apart from the first magnetized pole 320c and the second magnetized pole 320d by predetermined distances. The detector 320b is provided to detect the leakage magnetic flux due to an interior or surface defect of the steel plate 10 and may include a magnetic sensor or a hall sensor. Further, the detector 320b may be an array formed of a plurality of hall elements and an interval L between adjacent hall sensors HS1 and HS2 may be 60 μm or less. According to the exemplary embodiment of the present disclosure, the interval between the adjacent hall sensors HS1 and HS2 may be significantly reduced, defect detection may be further precisely performed.

Moreover, according to the exemplary embodiment of the present disclosure, the inspection units 320 may be provided in modular form and be individually detachable. In addition, the first magnetized pole 320c, the second magnetized pole 320d, the permanent magnet PM, and the detector 320b within each of the inspection units 320 may also be provided in modular form and the individual units may be separately detachable. The inspection device is provided in modular form as described above, maintenance and management efficiency of the inspection device may be increased.

Figure 4B:
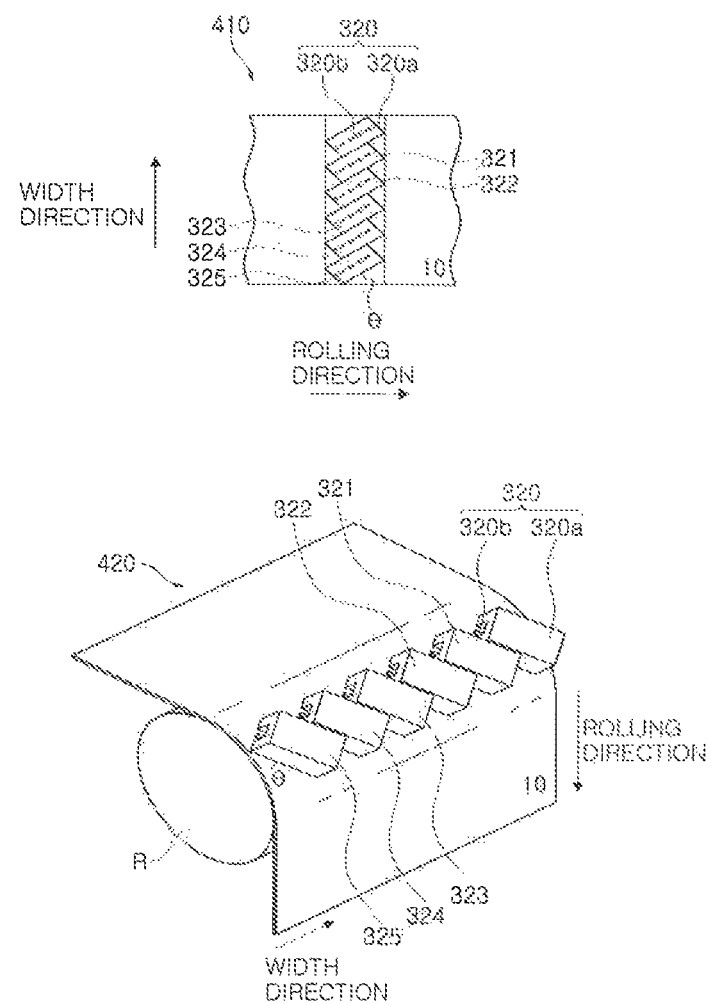
FIG. 4B is views illustrating a plurality of inspection units installed on a plane and an upper portion of a roll according to an exemplary embodiment of the present disclosure.
Figure 4C:
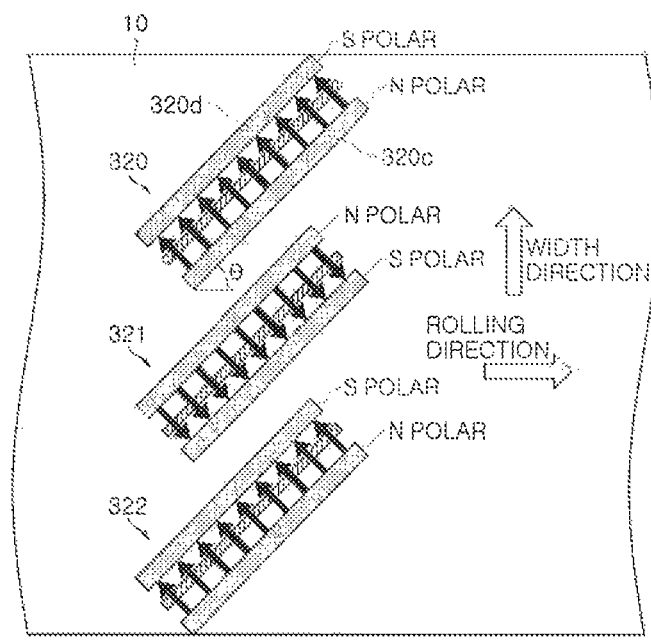
FIG. 4C is a view illustrating directions in which magnetized poles are disposed according to an exemplary embodiment of the present disclosure.

Meanwhile, FIG. 4B is views illustrating a plurality of inspection units installed on a plane and an upper portion of a roll according to an exemplary embodiment of the present disclosure. FIG. 4C is a view illustrating directions in which magnetized poles are disposed according to an exemplary embodiment of the present disclosure.

According to the exemplary embodiment of the present disclosure, as illustrated in reference numeral 410 of FIG. 4B, the defect inspection device for inspecting defects in the steel plate 10 (as described in detail with reference to FIG. 4A) may include a plurality of inspection units, and each of a plurality of inspection units 320 to 325 may be arranged in the width direction of the steel plate 10 and disposed in a direction inclined at a predetermined angle θ with respect to a rolling direction of the steel plate 10. The plurality of inspection units 320 to 325 may be spaced apart from the steel plate 10 by a predetermine distance in a vertical direction. Although FIG. 4B illustrates a case in which only six inspection units 320 to 325 are provided, the case is merely provided for the convenience of explanation and it may be apparent to a person having ordinary skill in the art that the number of inspection units may be variously modified as needed.

Furthermore, depending on embodiments, as illustrated in reference numeral 420 of FIG. 4B, the plurality of inspection units 320 to 325 may be arranged in the width direction of the steel plate 10 on the upper portion of the steel plate 10 wound around a surface of a roll R, but may be disposed in a direction inclined at a predetermined angle θ with respect to a rolling direction of the steel plate 10.

Hereinafter, directions in which magnetized poles within the inspection units are disposed will be described in detail with reference to FIG. 4C. For the understanding of the present disclosure, although FIG. 4C only illustrates three inspection units 320 to 322, the number of inspection units may be equal to the number of inspection units illustrated in FIG. 4B. In addition, for the understanding of the present disclosure, although the exemplary embodiment is explained based on a single inspection unit 320 with reference to FIG. 4C, the disposition directions may be applied to the remaining inspection units 321 and 322 in the same manner.

As illustrated in FIG. 4C, the first magnetized pole 320c and the second magnetized pole 320d may have opposite polarities. The second magnetized pole 320d may be spaced apart from the first magnetized pole 320c by a predetermined distance and disposed to be parallel thereto, in a direction perpendicular to a direction in which the first magnetized pole 320c is inclined, and the first magnetized pole 320c and the second magnetized pole 320d may have the same length. Here, an angle θ at which the first magnetized pole 320c and the second magnetized pole 320d are inclined with respect to the rolling direction may be 45 degrees. The angle as described above is merely provided by way of example, it may be apparent to a person having ordinary skill in the art that the angle is modified as needed.

As described above, according to an exemplary embodiment of the present disclosure, two magnetized poles 320c and 320d configuring the magnetizer 320a have the same length, directions and degrees of intensity of magnetic flux formed in both ends of the magnetized poles 320c and 320d may be uniform, such that accurate defect detection may be enabled.

An operational principle of the inspection device according to the exemplary embodiment as described above will be explained.

Referring to FIGS. 3 through 4C, power may be supplied to the detector 320b by the power supply unit 310 and the magnetic flux leakage caused by the defects D may be detected by the plurality of inspection units 320 to 325 arranged in the width direction of the steel plate 10. By way of example, in the single inspection unit 320, magnetic flux may be generated by the magnetizer 320a formed in a direction inclined at a predetermined angle with respect to the rolling direction, and the generated magnetic flux may pass through the steel plate 10. In this case, the detector 320b may detect a leakage magnetic flux due to the defects D present in the steel plate 10. The detected leakage magnetic flux may be transferred to the amplifier 330.

Next, the amplifier 330 may amplify the leakage magnetic flux detected in the inspection unit 320 at a predetermined ratio and then, transfer the amplified leakage magnetic flux to the defect detection unit 340. Finally, the defect detection unit 340 may detect the defects D in the steel plate 10 based on the leakage magnetic flux amplified by the amplifier 330.

Figure 5A:
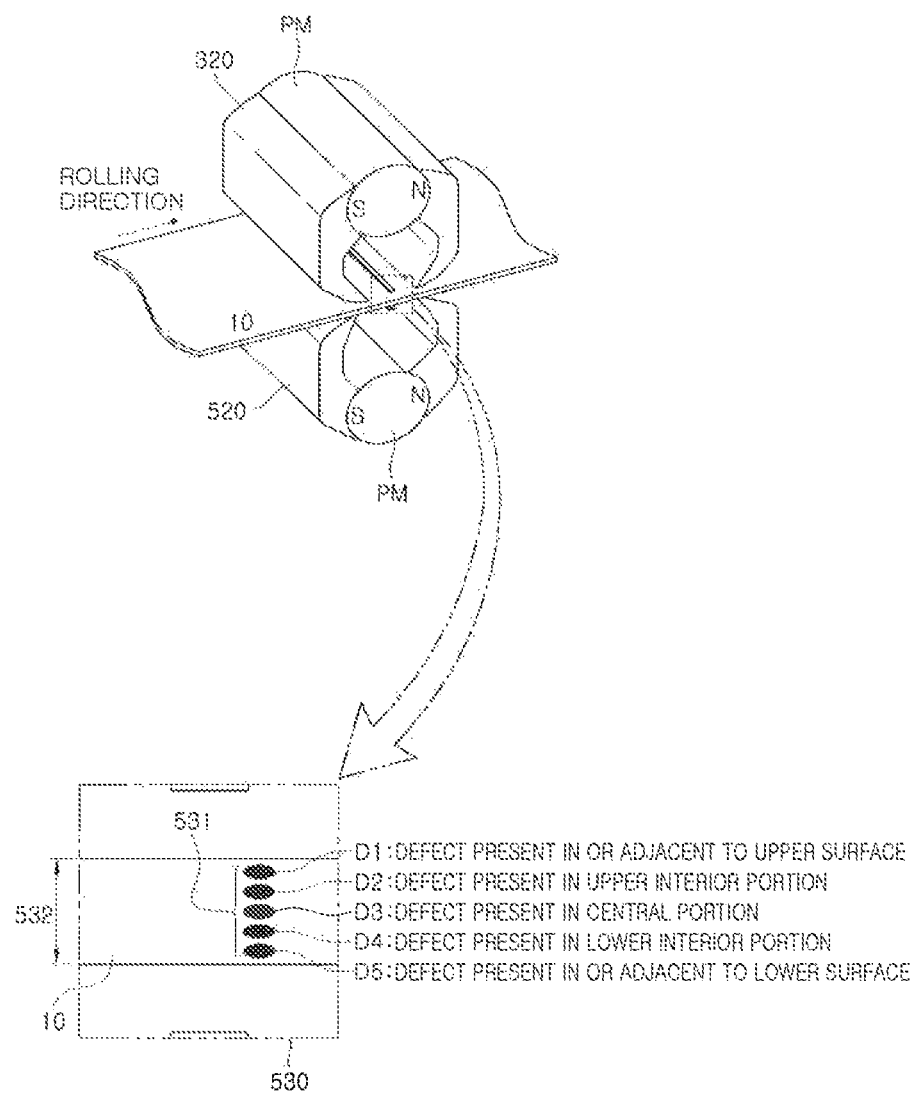
FIG. 5A is views illustrating inspection units disposed on upper and lower portions of a steel plate according to an exemplary embodiment of the present disclosure.
Figure 5B:
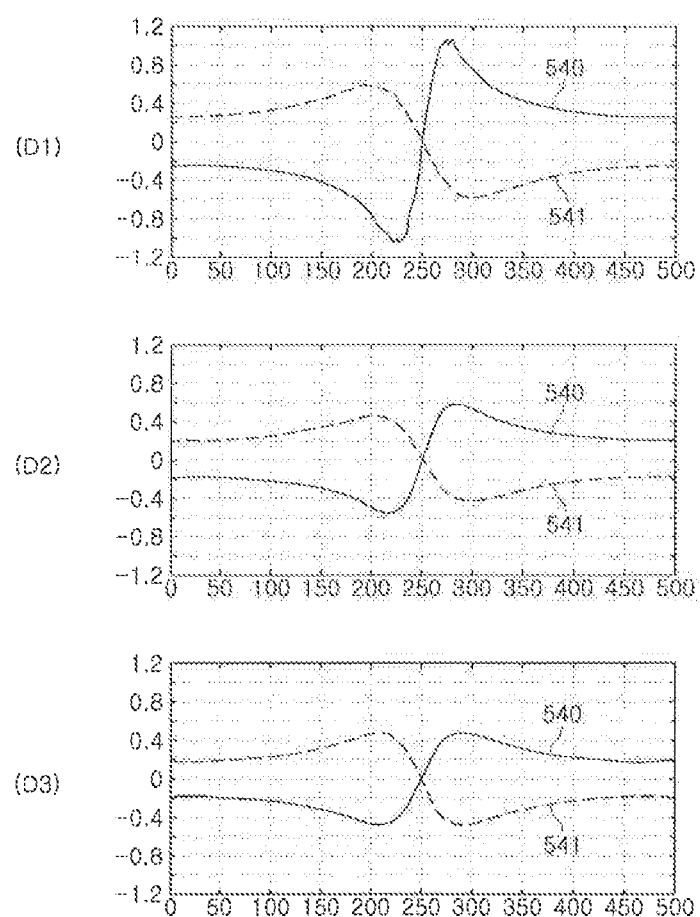
FIGS. 5B and 5C are diagrams illustrating output signals of the inspection units disposed on the upper and lower portions of the steel plate depending on positions of defects according to an exemplary embodiment of the present disclosure.
Figure 5C:
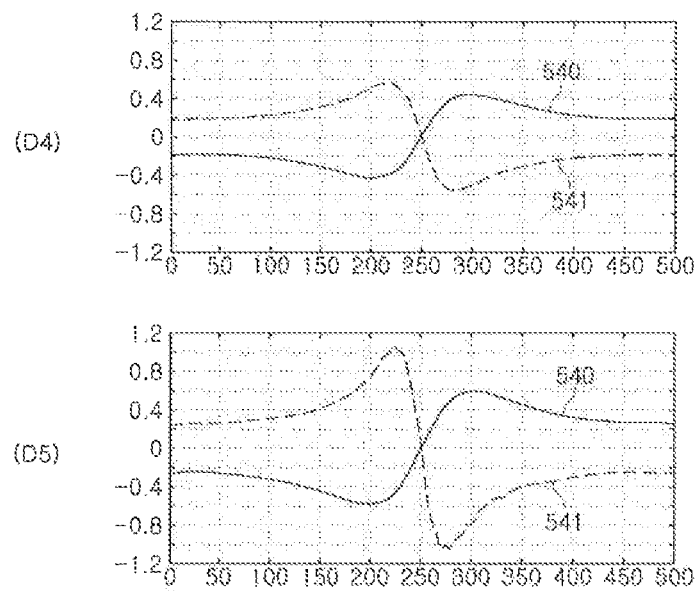

FIG. 5A is views illustrating inspection units disposed on upper and lower portions of a steel plate according to an exemplary embodiment of the present disclosure. Unlike FIG. 4A, a leakage magnetic flux may be detected by disposing inspection units 320 and 520 on both upper and lower portions of the steel plate 10, such that a surface defect and an interior defect may be separately detected or a position of the interior defect may be accurately determined. FIGS. 5B and 5C are diagrams illustrating output signals of the inspection units disposed on the upper and lower portions of the steel plate depending on positions of defects according to an exemplary embodiment of the present disclosure.

Hereinafter, an inspection device and an operational principle thereof according to an exemplary embodiment will be described.

Referring to FIG. 5A, an upper inspection unit 320 may be disposed on the upper portion of the steel plate 10 and a lower inspection unit 520 may be disposed on the lower portion of the steel plate 10, corresponding to the upper portion thereof. For the understanding of the present disclosure, while FIG. 5A illustrates a case in which a single upper inspection unit 320 and a single lower inspection unit 520 are disposed on the upper portion and the lower portion of the steel plate 10, respectively, a plurality of inspection units may be disposed on each of the upper and lower portions of the steel plate 10 as illustrated in FIG. 4B.

Meanwhile, reference numeral 530 indicates an enlarged view of defects present in a thickness direction of the steel plate 10, in an upper view of FIG. 5a and illustrates that the defects D may be present in various positions in a thickness direction 532 of the steel plate 10. For example, as illustrated in reference numeral 531, D1 indicates the defect D present in or adjacent to an upper surface of the steel plate 10, D2 indicates the defect D present in an upper interior portion, D3 indicates the defect D present in a central portion of the steel plate 10, D4 indicates the defect D present in a lower interior portion of the steel plate 10, and D5 indicates the defect D present in or adjacent to a lower surface of the steel plate 10.

With regard to the respective defects D1 to D5, output signals from the upper inspection unit 320 and the lower inspection unit 520 are illustrated in FIG. 5B and FIG. 5C, respectively. In FIGS. 5B and 5C, reference numeral 540 indicates an output signal from the upper inspection unit 320 and reference numeral 541 indicates an output signal from the lower inspection unit 520.

As illustrated in FIGS. 5B and 5C, magnitudes and phases of the output signals from the upper inspection unit 320 and the lower inspection unit 520 are different depending on positions of the defects D1 to D5. That is, in the case of the defect D1 formed in or adjacent to the upper surface of the steel plate 10, it can be seen that a phase of the output signal 540 from the upper inspection unit 320 is opposite to that of the output signal 541 from the lower inspection unit 520, and a magnitude of the output signal 540 from the upper inspection unit 320 is higher than that of the output signal 541 from the lower inspection unit 520. Thus, it can be seen that the defect D is formed in or adjacent to the upper surface of the steel plate 10.

On the contrary, in the case of the defect D5 formed in or adjacent to the lower surface of the steel plate 10, it can be seen that a phase of the output signal 541 from the lower inspection unit 520 is opposite to that of the output signal 540 from the upper inspection unit 320, and a magnitude of the output signal 541 from the lower inspection unit 520 is higher than that of the output signal 540 from the upper inspection unit 320. Thus, it can be seen that the defect D is formed in or adjacent to the lower surface of the steel plate 10.

On the other hand, in the case of the defect D3 formed in the central portion of the steel plate 10, it can be seen that the output signal 540 from the upper inspection unit 320 and the output signal 541 from the lower inspection unit 520 have the same degree of magnitude, but have opposite phases. Thus, it can be seen that the defect D is formed in the central portion of the steel plate 10.

As described above, the position of the defect D may be analyzed by comparing the phase and the magnitude of the output signal 540 from the upper inspection unit 320 with those of the output signal 541 from the lower inspection unit 520.

In addition to the graphical method described above, a defect position DP may be analyzed by calculating a defect function DF to which various factors are input, and a description thereof will be described with reference to FIGS. 5D and 5E.

Figure 5D:
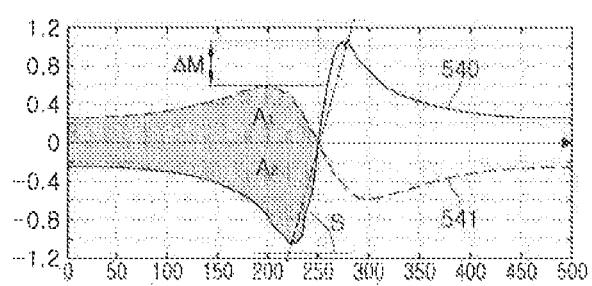
FIGS. 5D and 5E are diagrams for describing a method for analyzing the positions of defects from the output signals of the inspection units disposed on the upper and lower portions of the steel plate.

FIG. 5D is a diagram for describing factors provided to calculate the defect function DF from the output signal 540 from the upper inspection unit 320 and the output signal 541 from the lower inspection unit 520.

In FIG. 5D, $\Delta M$ denotes a difference in magnitudes of two output signals 540 and 541, A1 denotes an area of the output signal 541 from the lower inspection unit 520, A2 denotes an area of the output signal 540 from the upper inspection unit 320, and S denotes a slope of a straight line formed by connecting a maximum value and a minimum value of the output signal.

According to an exemplary embodiment of the present disclosure, the defect function DF may be calculated according to the following mathematical formula 1, based on several further factors in addition to the various factors described above.

$$DF = f(\Delta M, A, S, Wf, L)$$ [Mathematical Formula 1]

Here, DF denotes a defect function, $\Delta M$ denotes a difference in magnitudes of two output signals, A denotes an area of the output signal, S denotes a slope of a straight line formed by connecting a maximum value and a minimum value of the output signal, Wf denotes a defect type (an circle, an oval, a line or the like), and L denotes a value for compensating an interval between the detector and the steel plate.

The defect function DF to which the factors such as $\Delta M$, A, S, Wf, and L are input may be variously implemented, and it is not limited thereto in the present disclosure.

However, hereinafter, the defect function DF to which only $\Delta M$ among the above-described factors such as $\Delta M$, A, S, Wf, and L is input is calculated in FIG. 5E. A method of analyzing the defect position DP from the calculated defect function DF will be exemplified with reference to FIG. 5E. It is assumed that a thickness of the steel plate 10 is 1.2 mm and a distance from a surface of the steel plate 10 to a center thereof is 0.6 mm.

Figure 5E:
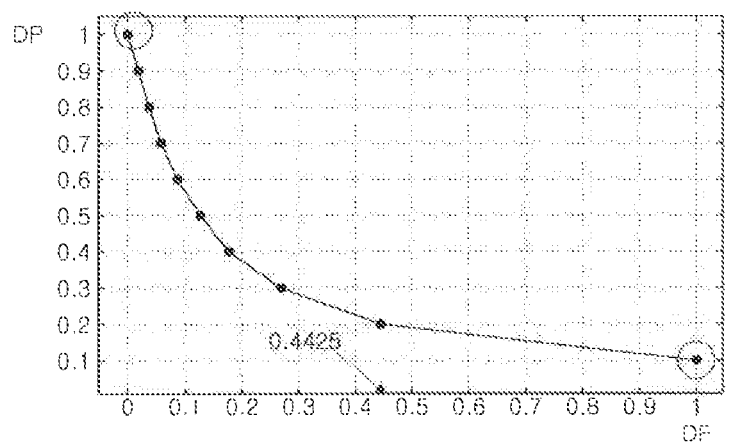

First, the defect detection unit 340 of FIG. 3 may calculate the difference $\Delta M$ in magnitudes of the two output signals 540 and 541 depending on the defect position DP from the surface of the steel plate 10 to the center thereof and subsequently, may obtain a graph as illustrated in FIG. 5E. Here, the defect position DP of 1 refers to a point distant from the upper surface of the steel plate 10 by 0.6 mm (that is, the center of the steel plate) and the defect position DP of 0.1 refers to a point, the upper surface of the steel plate 10.

Thereafter, the defect detection unit 340 of FIG. 3 may calculate the difference $\Delta M$ in magnitudes of the output signals 540 and 541 obtained from the upper inspection unit 320 and the lower inspection unit 520 and compare the calculated difference $\Delta M$ in magnitudes with the graph of FIG. 5E to thereby analyze the defect position DP.

For example, in FIG. 5E, in a case in which the difference $\Delta M$ (that is, the defect function DF) in magnitudes of the two output signals is 1 (when $\Delta M$ is 1, since the difference $\Delta M$ in magnitudes of the two output signals is the greatest, it may be previously confirmed that the defect D may be present in the upper surface of the steel plate 10), it can be confirmed that the defect position DP is 0.1 and accordingly, the defect D is located in the upper surface of the steel plate 10.

As another example, in a case in which the difference $\Delta M$ (that is, the defect function DF) in magnitudes of the two output signals is 0 (when $\Delta M$ is 0, since the difference $\Delta M$ in magnitudes of the two output signals is the lowest, it may be previously confirmed that the defect D may be present in the center of the steel plate 10), it can be confirmed that the defect position DP is 1 and accordingly, the defect D is located in the point (the center) distant from the upper surface of the steel plate 10 by 0.6 mm.

In a case in which the difference $\Delta M$ in magnitudes of the two output signals ranges from 1 to 0, it may be analyzed that the defect D may be present in a certain point between the upper surface of the steel plate 10 and the center thereof (the point distant from the upper surface of the steel plate 10 by 0.6 mm)

As set forth above, according to exemplary embodiments of the present disclosure, the inspection units may be disposed on both upper and lower portions of the steel plate to detect a leakage magnetic flux, such that a surface defect and an interior defect may be separately detected and a position of the interior defect may be accurately determined.

While the present disclosure has been shown and described in connection with the embodiments and the drawings, it will be apparent to those skilled in the art that modifications and variations can be made without departing from the spirit and scope of the disclosure as defined by the appended claims.

The invention claimed is:
1. A defect inspection device for inspecting defects in a steel plate, the defect inspection device comprising:

a plurality of upper and lower inspection units arranged in a width direction of the steel plate, the upper inspection units being disposed on an upper portion of the steel plate and the lower inspection units being disposed on a lower portion of the steel plate, wherein each of the inspection units includes:

a magnetizer including a first magnetized pole and a second magnetized pole corresponding to each other, and generating magnetic flux for magnetizing the steel plate in a direction inclined at a predetermined angle with respect to a rolling direction of the steel plate;

a detector detecting a leakage magnetic flux leaked due to defects present in an interior portion or a surface of the steel plate, using the magnetic flux generated by the magnetizer; and a defect detection unit detecting a defect position in a thickness direction of the steel plate, based on a phase and a magnitude of a signal measured by each of the upper inspection units and lower inspection units, the defect detection unit detecting defects using a defects function DF calculated according to the following formula: $DF=f(\Delta M, A, S, W_f, L)$, where DF denotes a defect function, $\Delta M$ denotes a difference in magnitudes of two output signals, A denotes an area of the output signal, S denotes a slope of a straight line formed by connecting a maximum value and a minimum value of the output signal, $W_f$ denotes a defect type, and L denotes a value for compensating an interval between the detector and the steel plate.

2. The defect inspection device of claim 1, wherein the second magnetized pole is spaced apart from the first magnetized pole by a predetermined distance and disposed to be parallel to the first magnetized pole, in a direction perpendicular to a direction in which the first magnetized pole is inclined.

3. The defect inspection device of claim 1, wherein the first magnetized pole and the second magnetized pole have the same length.

4. The defect inspection device of claim 1, wherein the first magnetized pole and the second magnetized pole are inclined at an angle of 45 degrees with respect to a rolling direction of the steel plate.

5. The defect inspection device of claim 1, wherein the plurality of inspection units are provided in modular form such that the inspection units are individually detachable.

6. The defect inspection device of claim 1, wherein:

the magnetizer has a permanent magnet and a yoke extended to first and second sides of the permanent magnet;

the first magnetized pole is provided on a first end of the yoke; and the second magnetized pole is provided on a second end of the yoke.

7. The defect inspection device of claim 6, wherein the permanent magnet is a cylindrical permanent magnet.

8. The defect inspection device of claim 7, wherein the cylindrical permanent magnet is provided in the magnetizer such that the cylindrical permanent magnet rotates about an axis of a cylinder extended in a length direction of the cylinder, and a magnitude of the magnetic flux included in the yoke is adjustable.

9. The defect inspection device of claim 1, wherein the detector includes a plurality of hall sensors, an interval between the hall sensors adjacent to each other being 60 μm or less.

* * * * *